(12) United States Patent
Nakai et al.

(10) Patent No.: US 9,045,591 B2
(45) Date of Patent: *Jun. 2, 2015

(54) METHOD FOR PRODUCING NYLON SALT POWDER, AND METHOD FOR PRODUCING NYLON

(75) Inventors: Makoto Nakai, Kyoto (JP); Mariko Morimoto, Kyoto (JP); Mitsuhiro Kawahara, Kyoto (JP)

(73) Assignee: UNITIKA LTD., Hyogo (JP)

(*) Notice: Subject to any disclaimer, the term of this patent is extended or adjusted under 35 U.S.C. 154(b) by 78 days.

This patent is subject to a terminal disclaimer.

(21) Appl. No.: 13/822,749

(22) PCT Filed: Nov. 17, 2011

(86) PCT No.: PCT/JP2011/076474
§ 371 (c)(1),
(2), (4) Date: Mar. 13, 2013

(87) PCT Pub. No.: WO2012/070457
PCT Pub. Date: May 31, 2012

(65) Prior Publication Data
US 2013/0172521 A1      Jul. 4, 2013

(30) Foreign Application Priority Data
Nov. 26, 2010 (JP) .................. 2010-263031

(51) Int. Cl.
*C08G 69/26* (2006.01)
*C08G 69/28* (2006.01)
(Continued)

(52) U.S. Cl.
CPC ............. *C08G 69/26* (2013.01); *C07C 51/41* (2013.01); *C08G 69/28* (2013.01); *C08G 69/30* (2013.01)

(58) Field of Classification Search
CPC ............. C08G 69/26–69/32; C07C 63/28; C07C 51/41; C07C 51/412; C07C 211/09–211/12
USPC ............ 562/480, 590; 564/372, 461, 511
See application file for complete search history.

(56) References Cited

U.S. PATENT DOCUMENTS 4,135,043 A * 1/1979 Kast et al. ............. 526/63
5,731,403 A   3/1998 Lang
(Continued)

FOREIGN PATENT DOCUMENTS

CN      1166845      12/1997
CN      1624021      6/2005
(Continued)

OTHER PUBLICATIONS

"dry, adj. and adv." OED Online. Oxford University Press, Sep. 2014. Web. Oct. 19, 2014.*
(Continued)

*Primary Examiner* — Rachel Kahn
(74) *Attorney, Agent, or Firm* — Fildes & Outland, P.C.

(57) ABSTRACT

Disclosed is a method for producing a nylon salt powder, wherein in the production of a nylon salt powder by allowing a dicarboxylic acid powder to react, the content of water is regulated to be 5% by mass or less in relation to the total amount of the dicarboxylic acid powder and a diamine, the dicarboxylic acid powder is beforehand heated to a temperature equal to or higher than melting point of the diamine and equal to or lower than the melting point of the dicarboxylic acid, and while this heating temperature is being maintained, the diamine is added to the dicarboxylic acid powder in such a way that the dicarboxylic acid powder maintains the condition of being in powder form.

6 Claims, 1 Drawing Sheet

(51) Int. Cl.
*C07C 51/41* (2006.01)
*C08G 69/30* (2006.01)

(56) References Cited

U.S. PATENT DOCUMENTS

| 5,801,278 | A | 9/1998 | Bletsos et al. |
| 7,053,171 | B2 | 5/2006 | Otaki et al. |
| 2004/0236068 | A1 | 11/2004 | Otaki et al. |
| 2013/0018166 | A1 | 1/2013 | Nakai et al. |

FOREIGN PATENT DOCUMENTS

| JP | 62-020527 | 1/1987 |
| JP | 10-509761 | 9/1998 |
| JP | 2001-200053 | 7/2001 |
| JP | 2001-348427 | 12/2001 |
| JP | 2005-002327 | 1/2005 |
| WO | 2011/118441 | 9/2011 |

OTHER PUBLICATIONS

"powder, n.1." OED Online. Oxford University Press, Sep. 2014. Web. Oct. 19, 2014.*

Supplementary European Search Report in application No. 11843585.8 dated Mar. 20, 2014.

* cited by examiner

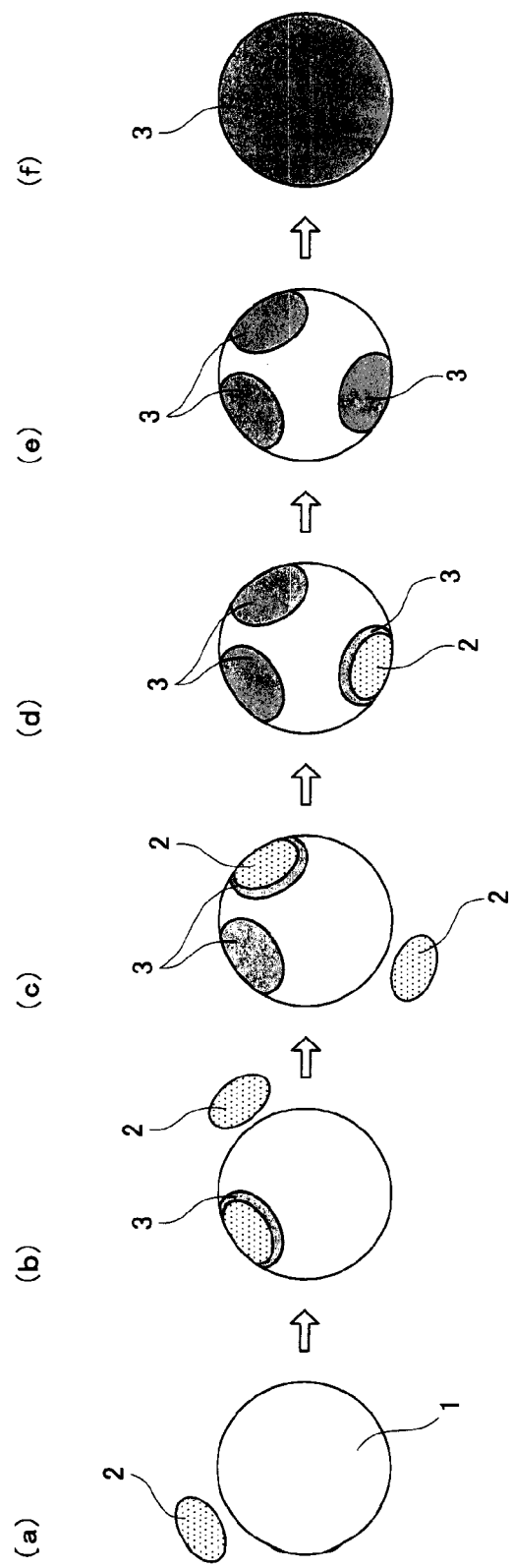

METHOD FOR PRODUCING NYLON SALT POWDER, AND METHOD FOR PRODUCING NYLON

TECHNICAL FIELD

The present invention relates to a method for producing a nylon salt powder suitable for the production of nylon excellent in heat resistance. Further, the present invention relates to a method for producing nylon, using the nylon salt powder obtained by the aforementioned production method.

BACKGROUND ART

The production of nylon excellent in heat resistance by using a diamine and a dicarboxylic acid as the starting materials has hitherto been investigated. A common method for producing nylon excellent in heat resistance by using a diamine and a dicarboxylic acid as the starting materials is as follows. Specifically, first, the diamine and the dicarboxylic acid are allowed to react to prepare a nylon salt. Then, the resulting nylon salt is subjected to solid phase polymerization or melt polymerization to achieve high molecular weight. By obtaining nylon from a nylon salt in such a way, it is possible to stably achieve high molecular weight of nylon.

Various methods for producing a nylon salt to be used for obtaining nylon have been investigated. For example, JP2001-348427A discloses a method for obtaining a nylon salt by allowing a diamine and a dicarboxylic acid to react with each other in the presence of water at a high temperature under a high pressure, and by subsequently blowing off the resulting reaction product at a high temperature to separate the water. However, as described above, the production method disclosed in JP2001-348427A requires a step of blowing off the diamine and the dicarboxylic acid having been allowed to react with each other at a high temperature under a high pressure. Accordingly, disadvantageously the production method disclosed in JP2001-348427A tends to involve large-scale production equipment, tends to involve cumbersome steps, or tends to lead to an increase in cost. Additionally, when nylon is produced by solid phase polymerization of the nylon salt obtained by using water, the resulting nylon gels, or a triamine having branched structure, a by-product, is produced. Consequently, disadvantageously, the melting point of the obtained nylon is decreased and the obtained nylon is poor in heat resistance. Under these circumstances, as a method for producing nylon, a polymerization method is regarded as ideal in which the powder of a nylon salt is obtained under the condition of absence of water, and the thus obtained nylon salt powder is polymerized.

On the other hand, JP2001-200053A discloses a production method in which a dicarboxylic acid is added to a molten diamine to prepare a slurry composed of the molten diamine and the solid dicarboxylic acid, and then the slurry is allowed to react to produce a nylon salt. However, in the production method disclosed in JP2001-200053A, the nylon salt is agglomerated in the reaction vessel, to make it difficult to take out the nylon salt from the reaction vessel. Additionally, even if the obtained nylon salt can be taken out from the reaction vessel, it is required to separately provide a step of pulverizing the agglomerated nylon salt when the nylon salt is allowed to be used actually, and hence the steps become complicated or cost increase may be caused.

In other words, it is the state-of-the art that a technique to obtain a nylon salt with a simple method under the condition of absence of water has never been found.

SUMMARY OF INVENTION

Technical Problem

For the purpose of solving such problems as described above, an object of the present invention is to efficiently obtain a powdery nylon salt under the conditions that the content of water is set at 5% by mass or less in relation to the total amount of the dicarboxylic acid powder and the diamine, and the dicarboxylic acid powder and the diamine are allowed to react with each other while the dicarboxylic acid powder is maintaining the condition of being in powder form. Another object of the present invention is to efficiently obtain nylon excellent in heat resistance and high in molecule weight by polymerizing the nylon salt in powder form.

Solution to Problem

Specifically, the gist of the present invention is as follows.

(1) A method for producing a nylon salt powder, wherein in the production of a nylon salt powder by allowing a dicarboxylic acid powder to react, the content of water is regulated to be 5% by mass or less in relation to the total amount of the dicarboxylic acid powder and a diamine, the dicarboxylic acid powder is beforehand heated to a temperature equal to or higher than the melting point of the diamine and equal to or lower than the melting point of the dicarboxylic acid, and while this heating temperature is being maintained, the diamine is added to the dicarboxylic acid powder in such a way that the dicarboxylic acid powder maintains the condition of being in powder form.

(2) The method for producing a nylon salt powder according to (1), wherein the heating temperature is set at 100 to 210° C.

(3) The method for producing a nylon salt powder according to (1) or (2), wherein the diamine heated to a temperature equal to or higher than the melting point of the diamine is sprayed and added in a spray-like form to the dicarboxylic acid powder.

(4) The method for producing a nylon salt powder according to any one of (1) to (3), wherein the dicarboxylic acid constituting the dicarboxylic acid powder is terephthalic acid and/or isophthalic acid.

(5) The method for producing a nylon salt powder according to any one of (1) to (4), wherein the addition rate of the diamine is 0.07 to 6.7% by mass/min in relation to the total amount of the diamine eventually added.

(6) A method for producing nylon wherein the nylon salt powder produced by the production method of any one of (1) to (5) is polymerized.

Advantageous Effects of Invention

According to the method for producing a nylon salt powder of the present invention, under the condition that the content of water is set at 5% by mass or less in relation to the total amount of the dicarboxylic acid powder and the diamine, the dicarboxylic acid powder and the diamine are allowed to react with each other while the dicarboxylic acid powder is maintaining the condition of being in powder form; and hence a powder nylon salt can be obtained without rendering the steps to become complicated or causing cost increase. Further, according to the method for producing nylon of the present invention, by polymerizing the nylon salt in powder form, nylon excellent in heat resistance and high in molecular weight can be efficiently obtained.

BRIEF DESCRIPTION OF DRAWING

FIG. 1 is a schematic view illustrating the cross sections of a diamine and a dicarboxylic acid powder during reaction, and the cross section of the produced nylon salt powder, in the production of the nylon salt powder of the present invention.

DESCRIPTION OF EMBODIMENTS

Hereinafter, the present invention is described.

The method for producing a nylon salt powder of the present invention uses a dicarboxylic acid powder and a diamine as the starting materials.

Examples of the dicarboxylic acid constituting the dicarboxylic acid powder include, without being particularly limited to: terephthalic acid, isophthalic acid, adipic acid, sebacic acid, oxalic acid, naphthalenedicarboxylic acid and cyclohexanedicarboxylic acid. Among these examples, from the viewpoint of the versatility, terephthalic acid, isophthalic acid and adipic acid are preferable; terephthalic acid and isophthalic acid are more preferable because terephthalic acid and isophthalic acid allow the melting point of the resulting nylon salt to be high so as to facilitate the maintenance of the state of being in a powder form and additionally allow the heat of reaction in the production of the salt to be made small.

The melting point of the dicarboxylic acid used in the present invention is usually approximately 120 to 400° C.

Examples of the diamine include, without being particularly limited to: 1,4-butanediamine, 1,6-hexanediamine, 1,9-nonanediamine, 1,10-decanediamine, 1,11-undecanediamine, 1,12-dodecanediamine, 2-methyl-1,5-pentanediamine, p-phenylenediamine, m-xylylenediamine and p-xylylenediamine. Among these examples, from the viewpoint of the versatility, 1,6-hexanediamine, 1,9-nonanediamine and 1,10-decanediamine are preferable.

The melting point of the diamine used in the present invention is usually approximately 25 to 200° C.

In the present invention, if necessary, by mixing lactams such as caprolactam with the nylon salt, a starting material of a copolymerized nylon can be prepared from the nylon salt. In the copolymerization of lactams with nylon, the amount of the copolymerized lactams may be set to fall within a range not impairing the advantageous effects of the present invention; for example, the amount of the copolymerized lactams is set preferably at 1 to 30 mol % and more preferably at 5 to 20 mol % in relation to the amount of the dicarboxylic acid.

Examples of the nylon salts obtained by combinations of such monomers as described above include: nylon salts to be used for obtaining nylons such as nylon 6T, nylon 9T, nylon 10T, nylon 6I, nylon 9I, nylon 10I, nylon 46, nylon 66, nylon 69, nylon 610, MXD6 nylon and PXD6 nylon. Herein, T, I, MXD and PXD represents terephthalic acid, isophthalic acid, m-xylylenediamine, and p-xylylenediamine, respectively.

Among these nylons, the method for producing a nylon salt powder of the present invention can be suitably used for the production of the nylon salts to be used for obtaining nylon 46, nylon 6T, nylon 9T and nylon 10T, which are nylons simultaneously having low water absorbing property, high heat resistance and high crystallinity in a manner well balanced therebetween.

The method for producing a nylon salt powder of the present invention requires the condition that a diamine is added to a dicarboxylic acid powder heated at a temperature equal to or higher than the melting point of the diamine and equal to or lower than the melting point of the dicarboxylic acid, and the diamine and the dicarboxylic acid powder are allowed to react with each other while the dicarboxylic acid powder is maintaining the condition of being in powder form.

The beforehand heating of the dicarboxylic acid powder offers an advantage such that the dicarboxylic acid is allowed to react with the diamine while the dicarboxylic acid powder is maintaining the condition of being in powder form. No beforehand heating of the dicarboxylic acid powder disadvantageously results in the agglomeration of the nylon salt. In other words, the heating of the dicarboxylic acid powder after the addition of the diamine does not allow, under the condition of insufficient temperature increase in the initial stage of heating, the diamine and the dicarboxylic acid to react with each other to result in no production of the nylon salt but in a mixture composed of the diamine liquid and the dicarboxylic acid powder, the mixture being in a slurry-like, paste-like, or clay-like condition. When the mixture is further heated from such a condition, no nylon salt in powder form but an agglomerated nylon salt is produced.

The dicarboxylic acid is required to maintain powder form at any stage during the reaction with the diamine. Accordingly, the dicarboxylic acid in an agglomerated condition is required to be used as a powder prepared by a technique such as pulverization.

For the purpose of allowing the dicarboxylic acid to maintain the condition of being in powder form at any stage during the reaction between the dicarboxylic acid and the diamine, the spreading of the added diamine in the reaction system is required not to cause a slurry-like, paste-like or clay-like condition of the whole reaction system. In this case, when the diamine is successively added, the diamine added in advance of the successive addition of the diamine is preferably allowed to react with the dicarboxylic acid maintaining the condition of being in powder form, to form a solid state. For the purpose of allowing the dicarboxylic acid and the obtained solid nylon salt to each maintain the condition of being in powder form, it is required to appropriately set the below-described conditions such as the addition amount, addition rate and addition method of the diamine, and the heating temperature of the dicarboxylic acid and reaction time of the dicarboxylic acid with the diamine, and it required to sufficiently stir the powder.

The reasons for the fact that by appropriately setting the aforementioned conditions, the condition of the dicarboxylic acid of being in powder form is allowed to be maintained are not yet clear, but are inferred as follows. In other words, by appropriately setting the aforementioned conditions, an appropriate amount of the diamine uniformly attaches to the surface of the dicarboxylic acid powder. Accordingly, it is inferred that the surface of the dicarboxylic acid powder and the surface of the nylon salt powder do not attach to each other to be allowed to be present independently of each other, and thus the agglomeration of the dicarboxylic acid powder and the nylon salt powder is suppressed.

In the present invention, to be a powder means to have a granular form, with the particle size of approximately 5 μm to 2 mm.

In the present invention, as described above, the condition of being in powder form of the dicarboxylic acid is maintained. The volume average particle size of the dicarboxylic acid is preferably 5 μm to 1 mm and more preferably 20 to 200 μm. The volume average particle size of dicarboxylic acid set at 5 μm to 1 mm enables the reaction of the nylon salt to proceed faster. Such a volume average particle size also alleviates the scattering of the powder so as to facilitate the handling of the powder. The method for determining the volume average particle size is described in detail in Examples.

Next, the formation reaction of the nylon salt powder in the method for producing a nylon salt powder of the present invention is described by using FIG. 1.

FIG. 1 is a schematic view illustrating the cross sections of a diamine and a dicarboxylic acid powder during the reaction, and the cross section of the produced nylon salt powder. (a) First, to the beforehand heated dicarboxylic acid powder 1, the diamine 2 is added. Then, (b) the reaction is started by bringing the diamine 2 into contact with a portion of the surface of the dicarboxylic acid powder 1, and (c) the nylon salt 3 is produced partially on the surface of the dicarboxylic acid powder 1. A further addition of the diamine 2 expands the diamine-attaching area on the surface of the dicarboxylic acid powder 1, and the reaction between the dicarboxylic acid powder 1 and the diamine 2 occurs successively. And, (d, e) the portion of the nylon salt 3 on the surface of the dicarboxylic acid powder 1 is increasingly expanded. On completion of the reaction between the dicarboxylic acid powder and the diamine, (f) a powder the whole of which is converted into a nylon salt is obtained.

The diamine may be added as a solid, or as a liquid after the diamine is heated and melted into a liquid; however, from the viewpoint of making smaller the volume average particle size of the obtained nylon salt powder, it is preferable to add the diamine after the diamine is heated and melted to be converted into a liquid.

When the diamine is added as a solid, the diamine is prepared in a vessel other than the reaction vessel, and the diamine may be added to the reaction vessel from the other vessel while the addition rate of the diamine is being regulated. The device for sending the diamine as a powder from the other vessel to the reaction vessel is preferably a device capable of sending the powder without being contaminated with the air in the atmosphere. Examples of such a device include a powder sending device equipped with a double damper structure. Additionally, when the diamine is added as a solid, by regulating the pressure in the other vessel in which the diamine is placed to be higher than the pressure in the reaction vessel, the backward flow of the diamine from the reaction vessel to the other vessel can be prevented.

On the other hand, when the diamine is added as a liquid, the diamine is heated and melted into a liquid in the vessel other than the reaction vessel and then conveyed into the reaction vessel, and the diamine in a liquid form is preferably sprayed and added in a spray-like form to the dicarboxylic acid powder. The device for sending the diamine as a liquid into the reaction vessel is preferably a device capable of sending the liquid without being contaminated with the air in the atmosphere. Additionally, when the liquid diamine is added, the outlet of the liquid sending device is preferably penetrated into the powder phase of the dicarboxylic acid to react with the diamine. In this way, the nylon salt powder can be efficiently prepared.

When the dicarboxylic acid powder and the diamine are allowed to react with each other, the molar ratio of the total feed amount of the dicarboxylic acid powder to the total feed amount of the diamine preferably falls within a range of (dicarboxylic acid powder)/(diamine)=45/55 to 55/45, and more preferably within a range of (dicarboxylic acid powder)/(diamine)=47.5/52.5 to 52.5/47.5. By controlling the molar ratio of the dicarboxylic acid powder to the diamine so as to fall within the aforementioned range, a nylon salt powder capable of producing a high molecular weight nylon can be produced.

In the method for producing a nylon salt powder of the present invention, when the starting materials are placed, the content of water is required to be 5% by mass or less, and is preferably 1% by mass or less, more preferably 0.5% by mass or less, furthermore preferably 0.3% by mass or less, particularly preferably 0.2% by mass or less and most preferably 0% by mass, in relation to the total amount of the starting materials, namely, the dicarboxylic acid powder and the diamine. If water is contained when the starting materials are placed, disadvantageously the produced nylon salt is partially melted to fuse or the pressure of the reaction system becomes high.

In the method for producing a nylon salt powder of the present invention, the dicarboxylic acid powder as a starting material is required to be beforehand heated before the addition of the diamine.

The heating temperature in the beforehand heating of the dicarboxylic acid powder as a starting material before the addition of the diamine is required to be set at a temperature equal to or higher than the melting point of the diamine and equal to or lower than the melting point of the dicarboxylic acid constituting the dicarboxylic acid powder, and is preferably set at a temperature equal to or higher than (the melting point of the diamine+10° C.) and equal to or lower than (the melting point of the dicarboxylic acid−5° C.). When the heating temperature is lower than the melting point of the diamine, the dicarboxylic acid powder and the diamine are both in a solid state, and thus, disadvantageously the formation reaction of the nylon salt is hardly allowed to proceed. On the other hand, the heating temperature exceeds the melting point of the dicarboxylic acid, the whole of the reaction system is liquefied, and disadvantageously the whole reaction system is agglomerated as the nylon salt is produced.

In the aforementioned heating temperature range, the heating temperature of the dicarboxylic acid powder is preferably 100° C. or higher and 210° C. or lower and more preferably 120° C. or higher and 200° C. or lower. When the heating temperature is lower than 100° C., the formation reaction of the nylon salt is sometimes insufficient. On the other hand, when the heating temperature exceeds 210° C., an amide formation reaction occurs to generate water during the formation reaction of the nylon salt, and consequently, due to the generated water, the obtained nylon salt is sometimes partially melted to cause fusion, or the pressure of the reaction system sometimes becomes high.

The heating temperature in the beforehand heating of the dicarboxylic acid powder as a starting material and the reaction temperature in the production of the nylon salt may be either the same temperature or different temperatures.

The reaction time in performing the formation reaction of the nylon salt is preferably 0 to 6 hours and more preferably 0.25 to 3 hours from the completion of the addition of the diamine, from the viewpoint of stably maintaining the condition of being in powder form of the dicarboxylic acid.

The addition method of the diamine is not particularly limited as long as the addition method is capable of maintaining the condition of being in powder form of the dicarboxylic acid during the reaction. Among such methods, from the viewpoint of suppressing the agglomeration of the obtained nylon salt and thus efficiently performing the formation reaction of the nylon salt, for example, the following methods are preferable: a method in which diamine is continuously added, or a method in which the diamine is intermittently added in a divided manner in an appropriate amount at a time (for example, at a time, in 1/10 to 1/100 the total amount of the diamine to be added). Alternatively, the diamine may be intermittently added in an appropriate amount at a time and subsequently the diamine may be added continuously. In other words, a combination of the forgoing methods is also preferable.

From the viewpoint of stably maintaining the condition of being in powder form of the dicarboxylic acid, the addition rate of the diamine is preferably 0.07 to 6.7% by mass/min and more preferably 0.1 to 3.4% by mass/min. Here, "% by mass/min" means the ratio of the amount of the diamine added in 1 minute to the total amount of the diamine added eventually.

From the viewpoint of making smaller the particle size of the obtained nylon salt powder, the addition time of the diamine is preferably 0.25 to 24 hours and more preferably 0.6 to 10 hours.

In the method for producing a nylon salt powder of the present invention, from the viewpoint of making efficient the formation reaction of the nylon salt, a terminal blocking agent or a polymerization catalyst may be added, within a range not imparting the advantageous effects of the present invention, in addition to the dicarboxylic acid powder and the diamine, when the starting materials are fed into the reaction vessel.

The terminal blocking agent is an agent to block the terminal of the terminal functional groups of a polymer. Examples of such a terminal blocking agent include acetic acid, lauric acid, benzoic acid, octylamine, cyclohexylamine and aniline. The amount used of the terminal blocking agent is preferably 5 mol % or less in relation to the total number of moles of the dicarboxylic acid powder and the diamine as the starting material monomers.

Examples of the polymerization catalyst include phosphoric acid, phosphorous acid, hypophosphorous acid, and the salts of these acids. The amount used of the polymerization catalyst is preferably 2 mol % or less in relation to the total number of moles of the dicarboxylic acid powder and the diamine as the starting material monomers because an excessive amount used of the polymerization catalyst causes the degradation of the performance or the workability of the product.

In the method for producing a nylon salt powder of the present invention, various additives may also be added at any stages of the production within ranges not impairing the advantageous effects of the present invention. Examples of such additives include an inorganic filling material, a filler and a stabilizer. The amount used of the additive(s) is preferably 20% by mass or less in relation to the total mass of the dicarboxylic acid powder and the diamine as the starting material monomers, from the viewpoint of not disturbing the contact between the dicarboxylic acid powder and the diamine.

In the method for producing a nylon salt powder of the present invention, the rate of formation of the nylon salt is preferably 90% or more and more preferably 95% or more. When the rate of formation of the nylon salt is 90% or more, the lost amount of the unreacted diamine as vapor through diffusion is decreased, to lead to an advantage of facilitating the yielding of a high molecular weight nylon. The method for determining the rate of formation of the nylon salt is described in detail in Examples.

The volume average particle size of the obtained nylon salt powder is preferably 2 mm or less and more preferably 500 μm or less. By setting the volume average particle size of the nylon salt at 2 mm or less, even when moisture is generated during the production of nylon by polymerizing the nylon salt powder, the escape of the moisture in the interior of the nylon salt is facilitated, to lead to an advantage of capable of increasing the rate of the amidation reaction.

In the method for producing a nylon salt powder of the present invention, for the purpose of completely performing the formation reaction of the nylon salt, the reaction mixture is preferably sufficiently stirred during the addition of the diamine and after the completion of the addition of the diamine. The stirring mechanism disposed in the reactor for allowing the dicarboxylic acid powder and the diamine to react with each other may be appropriately selected according to the type or the production amount of the produced nylon salt; examples of such a stirrer include a paddle type blender, a tumbler type blender and a ribbon type blender or mixer. The stirrer may also be combinations of these.

The reactor for allowing the dicarboxylic acid powder and the diamine to react with each other is not particularly limited as long as the reactor is capable of sufficiently stirring the dicarboxylic acid powder and the diamine; heretofore known reactors can be used as the foregoing reactor.

In the reactor, the method for heating the dicarboxylic acid powder before the reaction and the method for heating the reaction system in the formation reaction are not particularly limited; examples of such methods include the methods of heating by using a heating medium such as steam or by using a heater.

In the method for producing a nylon salt powder of the present invention, the reaction between the dicarboxylic acid powder and the diamine may be performed in the air, or in an atmosphere of an inert gas such as nitrogen. For the purpose of suppressing side reactions and coloration, the reaction between the dicarboxylic acid powder and the diamine is preferably performed in an inert gas atmosphere. The reaction can be performed under a sealed condition or in a flow of an inert gas.

In the method for producing a nylon salt powder of the present invention, the dicarboxylic acid powder and the diamine are allowed to react with each other at a temperature equal to or lower than the melting point of the dicarboxylic acid constituting the dicarboxylic acid powder, and hence the obtained nylon salt is not agglomerated and can be maintained in powder form. By maintaining the nylon salt in powder form, even when moisture is generated during the production of nylon by polymerizing the nylon salt, the escape of the moisture in the interior of the nylon salt is facilitated, and hence the rate of the amidation reaction can be increased; and additionally, the occurrence of triamine, which is a by-product having a branched structure, can be suppressed. Therefore, the method for producing a nylon salt powder of the present invention can be preferably used even in the case of producing a nylon salt to which it is difficult, due to the starting materials and the additives, to apply polymerization based on melt polymerization.

The method for producing a nylon salt powder of the present invention does not substantially use water, and hence it is not necessary to provide a step of distilling off water. Accordingly, as compared to the production method in which water is added, the method for producing for a nylon salt powder of the present invention can reduce the number of the steps.

Hereinafter, the method for producing nylon of the present invention is described.

Nylon can be obtained by polymerizing the nylon salt powder obtained by the foregoing method for producing a nylon salt powder.

The method for producing nylon of the present invention is not particularly limited as long as the production method is a method using the nylon salt powder obtained by the foregoing method for producing a nylon salt powder; as such a production method, the methods such as solid phase polymerization and melt polymerization can be used.

When nylon is produced by solid phase polymerization, the involved polymerization conditions are not particularly limited; however, the reaction temperature is set preferably at a temperature equal to or higher than 180° C. and equal to or lower than the melting point of nylon, and more preferably at a temperature equal to or higher than 200° C. and equal to or lower than the melting point of nylon. The reaction time can be set at 0.5 to 100 hours from the time at which the temperature reaches the reaction temperature, and is more preferably 0.5 to 24 hours. The solid phase polymerization may be performed in a flow of an inert gas such as nitrogen, or under reduced pressure. The solid polymerization may be performed stationarily or under stirring.

EXAMPLES

Next, the present invention is more specifically described by way of Examples. However, the present invention is not limited to these Examples.

The measurements of the physical properties of the nylon salt and nylon were performed by the following methods.

(1) The Condition of being in Powder Form of the Reactants

On completion of the addition of half the total amount of the diamine, the stirring blade was stopped and a valve (diameter: 50 mm) in the bottom section of the reactor was opened. Then, it was visually verified whether or not the reactants were discharged just by opening the valve. The case where the reactants were discharged, a small amount of the reactants was quickly sampled and the condition of being in powder of the sampled reactants was visually evaluated.

Good: Just the opening of the valve allowed the reactants to be discharged from the reactor. And, all the sampled reactants were in powder form.

Average: Just the opening of the valve allowed the reactants to be discharged from the reactor. However, the sampled reactants took a form of a mixture composed of substances in powder form and agglomerated substances.

Poor: Just the opening of the valve did not allow the reactants to be discharged from the reactor.

(2) The Condition of being in Powder Form of the Nylon Salt

After the completion of the reaction, the valve (diameter: 50 mm) in the bottom section of the reactor was opened. And, it was visually verified whether or not the nylon salt was discharged just by opening the valve. Then, in the case where the nylon salt was discharged, the condition of being in powder form of the obtained nylon salt was visually evaluated. The evaluation standards were the same as in the case of (1).

In the present invention, when both of the evaluations of (1) and (2) were "good" or "average," it was taken that the reaction occurred while the contents were maintaining the conditions of being in powder form.

(3) The Rate of Formation of the Nylon Salt

By using a differential scanning calorimeter (DSC-7, manufactured by Perkin-Elmer Corp.), under the conditions that the temperature was increased from 10° C. to 120° C. at a temperature increase rate of 20° C./min, the heat of fusion $\Delta H$ (J/g) of the unreacted diamine component, and the heat of fusion $\Delta H'$ (J/g) obtained by measuring only the diamine were derived. Then, the rate of formation of the nylon salt was determined by the following formula:

Rate of formation(%)=100−($\Delta H/\Delta H'$)×100

(4) The Volume Average Particle Size of the Powder

The volume average particle size of the powder was measured by using a laser diffraction/scattering particle size distribution analyzer (LA920, manufactured by Horiba, Ltd.).

(5) The Relative Viscosity of Nylon

Nylon was obtained by performing solid polymerization of 35 kg of the nylon salt in a 50-L reaction vessel, in a flow of nitrogen at a flow rate of 4 L/min, at 230° C. over 5 hours. The nylon was dissolved in 96% sulfuric acid to prepare a sample solution having a concentration of 1 g/dl. Successively, by using an Ubbelohde viscometer, the falling times of the sample solution and the solvent were measured at a temperature of 25° C., and the relative viscosity was determined by using the following formula:

Relative viscosity=(falling time of sample solution)/(falling time of only solvent)

Practically, the relative viscosity of 2.0 or more is preferable.

The starting materials used in Examples and Comparative Examples are as follows:

TPA: Terephthalic acid, melting point; 300° C. or higher, volume average particle size: 80 μm
ADA: Adipic acid, melting point: 152° C., volume average particle size: 170 μm
DA: 1,10-Decanediamine, melting point: 62° C.
HA: 1,6-Hexanediamine, melting point: 42° C.
BA: 1,4-Butanediamine, melting point: 27° C.
PA: p-Phenylenediamine, melting point: 139° C.
NA: 1,9-Nonanediamine, melting point: 36° C.
SHP: Sodium hypophosphite
BA: Benzoic acid Example 1

A mixture composed of 4.82 kg (29.0 mol) of TPA powder, 9.8 g (0.093 mol) of SHP as a polymerization catalyst and 77.9 g (0.64 mol) of BA as a terminal blocking agent was fed to a ribbon blender type reactor, and was heated to 180° C. under sealing with nitrogen and under stirring at a number of rotations of 30 rpm. Then, 5.10 kg (29.6 mol) of DA heated to 100° C. was continuously added at a rate of 0.56% by mass/min by using a liquid sending device, over 3 hours, to the TPA powder maintained at 180° C., to yield a nylon salt powder. The starting materials, reaction conditions and evaluation results of the obtained nylon salt powder are shown in Table 1.

TABLE 1

| | | | | Examples | | | | | | | |
|---|---|---|---|---|---|---|---|---|---|---|---|
| | | | | 1 | 2 | 3 | 4 | 5 | 6 | 7 | 8 |
| Starting materials | Dicarboxylic acid | Type | | TPA | TPA | ADA | ADA | TPA | TPA | TPA | ADA |
| | | Melting point | ° C. | >300 | >300 | 152 | 152 | >300 | >300 | >300 | 152 |
| | | Volume average particle size | μm | 80 | 80 | 170 | 170 | 80 | 80 | 80 | 170 |

TABLE 1-continued

|  |  |  | | | | | | | | | |
|---|---|---|---|---|---|---|---|---|---|---|---|
| | | Heating temperature | °C. | 180 | 145 | 125 | 125 | 95 | 215 | 180 | 125 |
| | Diamine | Type | | DA | HA | BA | BA | DA | DA | DA | HA |
| | | Melting point | °C. | 62 | 42 | 27 | 27 | 62 | 62 | 62 | 42 |
| | | Heating temperature | °C. | 100 | No heating | 60 | 60 | No heating | | 100 | No heating |
| Reaction conditions | Reaction temperature | | °C. | 180 | 145 | 125 | 125 | 95 | 215 | 180 | 125 |
| | Addition method of diamine | | | Continuous sending of liquid | Divided in 36 times | Continuous spraying | Continuous sending of liquid | Divided in 36 times | Divided in 36 times | Continuous spraying | Divided in 36 times |
| | Addition rate of diamine | | mass %/min | 0.56 | — | 0.83 | 0.56 | — | — | 0.56 | — |
| | Addition time of diamine | | hr | 3 | 3 | 2 | 3 | 3 | 3 | 3 | 3 |
| | Reaction time after addition of diamine | | hr | 0 | 1 | 1 | 1 | 1 | 1 | 0 | 1 |
| | Addition amount of water | | mass % | 0 | 0 | 0 | 0 | 0 | 0 | 0 | 0 |
| | Dicarboxylic acid/diamine (molar ratio) | | | 49/51 | 50/50 | 50/50 | 50/50 | 50/50 | 50/50 | 49/51 | 49/51 |
| | Condition of being in powder form of reactants during reaction | | | Good | Good | Good | Good | Good | Average | Good | Good |
| Evaluation results | Rate of formation | | % | 95 | 92 | 97 | 93 | 96 | 90 | 98 | 97 |
| | Volume average particle size of nylon salt | | μm | 135 | 224 | 120 | 202 | 250 | 1188 | 125 | 234 |
| | Condition of being in powder form of nylon salt | | | Good | Good | Good | Good | Good | Average | Good | Good |
| | Relative viscosity of nylon | | | 2.67 | 2.56 | 2.89 | 2.87 | 2.43 | 2.45 | 2.66 | 2.52 |

|  |  |  | | Examples | | | | | | |
|---|---|---|---|---|---|---|---|---|---|---|
| | | | | 9 | 10 | 11 | 12 | 13 | 14 | 15 |
| Starting materials | Dicarboxylic acid | Type | | TPA | TPA | TPA | TPA | TPA | ADA | ADA |
| | | Melting point | °C. | >300 | >300 | >300 | >300 | >300 | 152 | 152 |
| | | Volume average particle size | μm | 80 | 80 | 80 | 80 | 80 | 170 | 170 |
| | | Heating temperature | °C. | 175 | 180 | 180 | 180 | 180 | 125 | 125 |
| | Diamine | Type | | PA | DA | DA | DA | DA | HA | HA |
| | | Melting point | °C. | 139 | 62 | 62 | 62 | 62 | 42 | 42 |
| | | Heating temperature | °C. | | | | No heating | | | |
| Reaction conditions | Reaction temperature | | °C. | 175 | 180 | 180 | 180 | 180 | 125 | 125 |
| | Addition method of diamine | | | Divided in 36 times | Divided in 10 times | Divided in 36 times | Divided in 36 times | Divided in 36 times | Divided in 36 times | Divided in 36 times |
| | Addition rate of diamine | | mass %/min | — | — | — | — | — | — | — |
| | Addition time of diamine | | hr | 6 | 0.5 | 12 | 3 | 3 | 3 | 3 |
| | Reaction time after addition of diamine | | hr | 1 | 1 | 1 | 1 | 1 | 1 | 1 |
| | Addition amount of water | | mass % | 0 | 0 | 0 | 0 | 0 | 2 | 5 |
| | Dicarboxylic acid/diamine (molar ratio) | | | 50/50 | 50/50 | 50/50 | 44/56 | 56/44 | 49/51 | 49/51 |
| | Condition of being in powder form of reactants during reaction | | | Good | Average | Good | Average | Good | Good | Average |

TABLE 1-continued

| | | | | | | | | | | |
|---|---|---|---|---|---|---|---|---|---|---|
| Evaluation results | Rate of formation | % | 94 | 92 | 99 | 91 | 99 | 98 | 97 |
| | Volume average particle size of nylon salt | μm | 266 | 1222 | 141 | 233 | 131 | 246 | 342 |
| | Condition of being in powder form of nylon salt | | Good | Average | Good | Good | Good | Good | Good |
| | Relative viscosity of nylon | | — | 2.38 | 2.70 | 2.12 | 2.01 | 2.54 | 2.48 |

| | | | | Examples | | | | | | |
|---|---|---|---|---|---|---|---|---|---|---|
| | | | | 16 | 17 | 18 | 19 | 20 | 21 | 22 |
| Starting materials | Dicarboxylic acid | Type | | TPA | TPA | TPA | TPA | TPA | TPA | TPA |
| | | Melting point | °C | >300 | >300 | >300 | >300 | >300 | >300 | >300 |
| | | Volume average particle size | μm | 80 | 80 | 80 | 80 | 80 | 80 | 80 |
| | | Heating temperature | °C | 170 | 180 | 180 | 180 | 180 | 180 | 180 |
| | Diamine | Type | | NA | DA | DA | DA | DA | DA | DA |
| | | Melting point | °C | 36 | 62 | 62 | 62 | 62 | 62 | 62 |
| | | Heating temperature | °C | 80 | 100 | 100 | 100 | 100 | 100 | 100 |
| Reaction conditions | Reaction temperature | | °C | 170 | 180 | 180 | 180 | 180 | 180 | 180 |
| | Addition method of diamine | | | Continuous sending of liquid | Continuous sending of liquid | Continuous sending of liquid | Continuous sending of liquid | Continuous sending of liquid | Continuous sending of liquid | Continuous sending of liquid |
| | Addition rate of diamine | | mass %/min | 0.56 | 0.56 | 0.56 | 0.56 | 0.56 | 0.56 | 0.56 |
| | Addition time of diamine | | hr | 3 | 3 | 3 | 3 | 3 | 3 | 3 |
| | Reaction time after addition of diamine | | hr | 0 | 0 | 0 | 0 | 0 | 0 | 0 |
| | Addition amount of water | | mass % | 0 | 0.2 | 0.3 | 0.5 | 1.0 | 0 | 0 |
| | Dicarboxylic acid/diamine (molar ratio) | | | 49/51 | 49/51 | 49/51 | 49/51 | 49/51 | 49/51 | 49/51 |
| | Condition of being in powder form of reactants during reaction | | | Good | Good | Good | Good | Good | Good | Good |
| Evaluation results | Rate of formation | | % | 96 | 95 | 95 | 95 | 95 | 94 | 98 |
| | Volume average particle size of nylon salt | | μm | 144 | 135 | 155 | 185 | 201 | 167 | 131 |
| | Condition of being in powder form of nylon salt | | | Good | Good | Good | Good | Good | Good | Good |
| | Relative viscosity of nylon | | | 2.51 | 2.67 | 2.66 | 2.66 | 2.62 | 2.20 | 3.22 |

Example 2

To a reactor equipped with a paddle-type stirring blade, 1177 g (7.08 mol) of TPA powder was fed, and heated to 145° C. under sealing with nitrogen and under stirring at a number of rotations of 60 rpm. Then, 824 g (7.08 mol) of HA was added in an amount of 22.9 g once per 5 minutes (2.8% by mass per once), in 36 times (in other words, intermittently, 1/36 the total amount of HA at a time), to the TPA powder maintained at 145° C. by using a powder sending device equipped with a double damper structure while the condition of the sealing with nitrogen was being maintained. Then, further for 1 hour, the stirring was continued at 145° C. to yield a nylon salt powder. The starting materials, reaction conditions and evaluation results of the obtained nylon salt powder are shown in Table 1.

Example 3

To a ribbon blender type reactor, 6.32 kg (43.2 mol) of ADA powder was fed, and heated to 125° C. under sealing with nitrogen and under stirring at a number of rotations of 30 rpm. Then, 3.68 kg (43.2 mol) of BD heated to 60° C. was continuously added over 2 hours, while being sprayed in a spray form by using a sprayer, to the ADA powder maintained at 125° C. at a rate of 0.83% by mass/min. Then, further for 1 hour, the stirring was continued at 125° C. to yield a nylon salt powder. The starting materials, reaction conditions and evaluation results of the obtained nylon salt powder are shown in Table 1.

Example 4

A nylon salt powder was obtained by performing the same operations as in Example 1 except that BD was continuously added to an ADA powder at a rate of 0.56% by mass/min over 3 hours as shown in Table 1. The starting materials, reaction conditions and evaluation results of the obtained nylon salt powder are shown in Table 1.

Example 5

To a reactor equipped with a paddle-type stirring blade, 981.7 g (5.91 mol) of TPA powder was fed, and heated to 95° C. in a flow of nitrogen, under stirring at a number of rotations of 60 rpm. Then, 1018.3 g (5.91 mol) of DA was added in an amount of 28.286 g once per 5 minutes (2.8% by mass per once), divided in 36 times, to the TPA powder maintained at 95° C. by using a powder sending device equipped with a double damper structure while the condition of the sealing with nitrogen was being maintained. Then, further for 1 hour, the stirring was continued at 95° C. to yield a nylon salt powder. The starting materials, reaction conditions and evaluation results of the obtained nylon salt powder are shown in Table 1.

Example 6

A nylon salt powder was obtained by performing the same operations as in Example 5 except that the heating temperature of the TPA powder and the reaction temperature were altered to 215° C. The starting materials, reaction conditions and evaluation results of the obtained nylon salt powder are shown in Table 1.

Example 7

To a ribbon blender type reactor, a mixture composed of 4.82 kg (29.0 mol) of TPA powder, 9.8 g (0.093 mol) of SHP as a polymerization catalyst and 77.9 g (0.64 mol) of BA as a terminal blocking agent was fed, and heated to 180° C. under sealing with nitrogen and under stirring at a number of rotations of 30 rpm. Then, 5.10 kg (29.6 mol) of DA heated to 100° C. was continuously sprayed in a spray form over 3 hours by using a sprayer, to the mixture maintained at 180° C. at a rate of 0.56% by mass/min, to yield a nylon salt powder. The starting materials, reaction conditions and evaluation results of the obtained nylon salt powder are shown in Table 1.

Example 8

To a reactor equipped with a paddle-type stirring blade, 1094.3 g (7.49 mol) of ADA powder was fed, and heated to 125° C. in a flow of nitrogen, under stirring at a number of rotations of 60 rpm. Then, 905.7 g (7.79 mol) of HA was added in an amount of 25.158 g once per 5 minutes (2.8% by mass per once), divided in 36 times, to the ADA powder maintained at 125° C. by using a powder sending device equipped with a double damper structure while the condition of the sealing with nitrogen was being maintained. Then, further for 1 hour, the stirring was continued at 125° C. to yield a nylon salt powder. The starting materials, reaction conditions and evaluation results of the obtained nylon salt powder are shown in Table 1.

Example 9

To a reactor equipped with a paddle-type stirring blade, 1211.4 g (7.29 mol) of TPA powder was fed, and heated to 175° C. in a flow of nitrogen, under stirring at a number of rotations of 60 rpm. Then, 788.6 g (7.29 mol) of PA was added in an amount of 21.905 g once per 10 minutes (2.8% by mass per once), divided in 36 times, to the TPA powder maintained at 175° C. by using a powder sending device equipped with a double damper structure while the condition of the sealing with nitrogen was being maintained. Then, further for 1 hour, the stirring was continued at 175° C. to yield a nylon salt powder. The starting materials, reaction conditions and evaluation results of the obtained nylon salt powder are shown in Table 1. By an IR measurement with an infrared spectrophotometer (Model: System 2000, manufactured by Perkin-Elmer Corp.), the polymerized product was verified to be p-aramid.

Example 10

To a reactor equipped with a paddle-type stirring blade, 981.7 g (5.91 mol) of TPA powder was fed, and heated to 180° C. in a flow of nitrogen, under stirring at a number of rotations of 60 rpm. Then, 1018.3 g (5.91 mol) of DA was added in an amount of 101.83 g once per 3 minutes (10.0% by mass per once), divided in 10 times, to the TPA powder maintained at 180° C. by using a powder sending device equipped with a double damper structure while the condition of the sealing with nitrogen was being maintained. Then, further for 1 hour, the stirring was continued at 180° C. to yield a nylon salt powder. The starting materials, reaction conditions and evaluation results of the obtained nylon salt powder are shown in Table 1.

Example 11

To a reactor equipped with a paddle-type stirring blade, 981.7 g (5.91 mol) of TPA powder was fed, and heated to 180° C. in a flow of nitrogen, under stirring at a number of rotations of 60 rpm. Then, 1018.3 g (5.91 mol) of DA was added in an amount of 28.286 g once per 20 minutes (2.8% by mass per once), divided in 36 times, to the TPA powder maintained at 180° C. by using a powder sending device equipped with a double damper structure while the condition of the sealing with nitrogen was being maintained. Then, further for 1 hour, the stirring was continued at 180° C. to yield a nylon salt powder. The starting materials, reaction conditions and evaluation results of the obtained nylon salt powder are shown in Table 1.

Example 12

To a reactor equipped with a paddle-type stirring blade, 862.0 g (5.19 mol) of TPA powder was fed, and heated to 180° C. in a flow of nitrogen, under stirring at a number of rotations of 60 rpm. Then, 1138.0 g (6.60 mol) of DA was added in an amount of 31.627 g once per 5 minutes (2.8% by mass per once), divided in 36 times, to the TPA powder maintained at 180° C. by using a powder sending device equipped with a double damper structure while the condition of the sealing with nitrogen was being maintained. Then, further for 1 hour, the stirring was continued at 180° C. to yield a nylon salt powder. The starting materials, reaction conditions and evaluation results of the obtained nylon salt powder are shown in Table 1.

Example 13

To a reactor equipped with a paddle-type stirring blade, 1102.0 g (6.63 mol) of TPA powder was fed, and heated to 180° C. in a flow of nitrogen, under stirring at a number of rotations of 60 rpm. Then, 898.0 g (5.21 mol) of DA was added in an amount of 24.944 g once per 5 minutes (2.8% by mass per once), divided in 36 times, to the TPA powder maintained at 180° C. by using a powder sending device equipped with a double damper structure while the condition of the sealing with nitrogen was being maintained. Then, further for 1 hour, the stirring was continued at 180° C. to yield a nylon salt powder. The starting materials, reaction conditions and evaluation results of the obtained nylon salt powder are shown in Table 1.

Example 14

To a reactor equipped with a paddle-type stirring blade, 1094.3 g (7.49 mol) of ADA powder and 40 g of water (2% by mass in relation to the total amount of the dicarboxylic acid powder and the diamine) were fed, and heated to 125° C. in a flow of nitrogen, under stirring at a number of rotations of 60 rpm. Then, 905.7 g (7.79 mol) of HA was added in an amount of 25.158 g once per 5 minutes (2.8% by mass per once), divided in 36 times, to the ADA powder maintained at 125° C. by using a powder sending device equipped with a double damper structure while the condition of the sealing with nitrogen was being maintained. Then, further for 1 hour, the stirring was continued at 125° C. to yield a nylon salt powder. The starting materials, reaction conditions and evaluation results of the obtained nylon salt powder are shown in Table 1.

Example 15

To a reactor equipped with a paddle-type stirring blade, 1094.3 g (7.49 mol) of ADA powder and 100 g of water (5% by mass in relation to the total amount of the dicarboxylic acid powder and the diamine) were fed, and heated to 125° C. in a flow of nitrogen, under stirring at a number of rotations of 60 rpm. Then, 905.7 g (7.79 mol) of HA was added in an amount of 25.158 g once per 5 minutes (2.8% by mass per once), divided in 36 times, to the ADA powder maintained at 125° C. by using a powder sending device equipped with a double damper structure while the condition of the sealing with nitrogen was being maintained. Then, further for 1 hour, the stirring was continued at 125° C. to yield a nylon salt powder. The starting materials, reaction conditions and evaluation results of the obtained nylon salt powder are shown in Table 1.

Example 16

To a ribbon blender type reactor, a mixture composed of 5.03 kg (30.2 mol) of TPA powder, 10.3 g (0.097 mol) of SHP as a polymerization catalyst and 81.3 g (0.67 mol) of BA as a terminal blocking agent was fed, and heated to 170° C. under sealing with nitrogen and under stirring at a number of rotations of 30 rpm. Then, 4.88 kg (30.9 mol) of NA heated to 80° C. was added continuously to the mixture maintained at 170° C. by using a liquid sending device, at a rate of 0.56% by mass/min over 3 hours, and thus a nylon salt powder was obtained. The starting materials, reaction conditions and evaluation results of the obtained nylon salt powder are shown in Table 1.

Example 17

A nylon salt powder was obtained in the same manner as in Example 1 except that in addition to the dicarboxylic acid powder and the diamine, 19.84 g of water (0.2% by mass in relation to the total amount of the dicarboxylic acid powder and the diamine) was fed to the reactor. The starting materials, reaction conditions and evaluation results of the obtained nylon salt powder are shown in Table 1.

Example 18

A nylon salt powder was obtained in the same manner as in Example 1 except that in addition to the dicarboxylic acid powder and the diamine, 29.76 g of water (0.3% by mass in relation to the total amount of the dicarboxylic acid powder and the diamine) was fed to the reactor. The starting materials, reaction conditions and evaluation results of the obtained nylon salt powder are shown in Table 1.

Example 19

A nylon salt powder was obtained in the same manner as in Example 1 except that in addition to the dicarboxylic acid powder and the diamine, 49.6 g of water (0.5% by mass in relation to the total amount of the dicarboxylic acid powder and the diamine) was fed to the reactor. The starting materials, reaction conditions and evaluation results of the obtained nylon salt powder are shown in Table 1.

Example 20

A nylon salt powder was obtained in the same manner as in Example 1 except that in addition to the dicarboxylic acid powder and the diamine, 99.2 g of water (1.0% by mass in relation to the total amount of the dicarboxylic acid powder and the diamine) was fed to the reactor. The starting materials, reaction conditions and evaluation results of the obtained nylon salt powder are shown in Table 1.

Example 21

To a ribbon blender type reactor, a mixture composed of 4.82 kg (29.0 mol) of TPA powder and 77.9 g (0.64 mol) of BA as a terminal blocking agent was fed, and heated to 180° C. under sealing with nitrogen and under stirring at a number of rotations of 30 rpm. Then, 5.10 kg (29.6 mol) of DA heated to 100° C. was added continuously to the TPA powder maintained at 180° C. by using a liquid sending device, at a rate of 0.56% by mass/min over 3 hours, and thus a nylon salt powder was obtained. The starting materials, reaction conditions and evaluation results of the obtained nylon salt powder are shown in Table 1.

Example 22

A nylon salt powder was obtained in the same manner as in Example 21 except that a mixture composed of 4.82 kg (29.0 mol) of TPA powder and 9.8 g (0.093 mol) of SHP as a polymerization catalyst was fed to the reactor. The starting materials, reaction conditions and evaluation results of the obtained nylon salt powder are shown in Table 1.

Comparative Example 1

To a reactor equipped with a paddle-type stirring blade, 1177 g (7.08 mol) of TPA powder was fed, and heated to 145° C. under sealing with nitrogen and under stirring at a number of rotations of 60 rpm. Then, 823 g (7.08 mol) of HA was added in a lump to the TPA powder maintained at 145° C. Then, further for 4 hours, the stirring was continued at 145° C.

The TPA undergoing the reaction agglomerated in the reactor. The starting materials, reaction conditions and evaluation results of the nylon salt are shown in Table 2.

TABLE 2

|  |  |  |  | Comparative Examples | | | |
|---|---|---|---|---|---|---|---|
|  |  |  |  | 1 | 2 | 3 | 4 |
| Starting materials | Dicarboxylic acid | Type |  | TPA | ADA | ADA | ADA |
|  |  | Melting point | °C. | >300 | 152 | 152 | 152 |
|  |  | Volume average particle size | μm | 80 | 170 | 170 | 170 |
|  |  | Heating temperature | °C. | 145 | 165 | No heating | 125 |
|  | Diamine | Type |  | HA | BA | BA | HA |
|  |  | Melting point | °C. | 42 | 27 | 27 | 42 |
|  |  | Heating temperature | °C. |  | No heating | | |
| Reaction conditions | Reaction temperature |  | °C. | 145 | 165 | 165 | 125 |
|  | Addition method of diamine |  |  | Once in a lump | Continuous liquid sending | Continuous liquid sending | Divided in 36 times |
|  | Addition rate of diamine |  | mass %/min | — | 0.56 | 0.56 | — |
|  | Addition time of diamine |  | hr | 0 | 3 | 3 | 3 |
|  | Reaction time after addition of diamine |  | hr | 4 | 1 | 1 | 1 |
|  | Addition amount of water |  | mass % | 0 | 0 | 0 | 7 |
|  | Dicarboxylic acid/diamine (molar ratio) |  |  | 50/50 | 50/50 | 50/50 | 49/51 |
|  | Condition of being in powder form of reactants during reaction |  |  | Poor | Poor | Poor | Poor |
| Evaluation results | Rate of formation |  | % | 69 | 57 | 81 | 99 |
|  | Volume average particle size of nylon salt |  | μm | No measurement (agglomerated) | | No measurement (admixture of agglomerate and powder) | |
|  | Condition of being in powder form of nylon salt |  |  | Poor | Poor | Poor | Poor |
|  | Relative viscosity of nylon |  |  | 1.79 | 1.44 | 1.92 | 2.45 |

Comparative Example 2

A nylon salt was obtained by performing the same operations as in Example 4 except that the heating temperature of the ADA powder and the reaction temperature were set at 165° C. The obtained nylon salt agglomerated in the reactor. The starting materials, reaction conditions and evaluation results of the nylon salt are shown in Table 2.

Comparative Example 3

A nylon salt was obtained by performing the same operations as in Example 4 except that the ADA powder was not beforehand heated. The obtained nylon salt was an admixture of agglomerate and powder. The starting materials, reaction conditions and evaluation results of the obtained nylon salt are shown in Table 2.

Comparative Example 4

To a reactor equipped with a paddle-type stirring blade, 1094.3 g (7.49 mol) of ADA powder and 140 g of water (7% by mass in relation to the total amount of the dicarboxylic acid powder and the diamine) were fed, and heated to 125° C. in a flow of nitrogen, under stirring at a number of rotations of 60 rpm. Then, while the temperature was being maintained at 125° C., 905.7 g (7.79 mol) of HA was added in an amount of 25.158 g once per 5 minutes (2.8% by mass per once), divided in 36 times, to the TPA powder. Further, for 1 hour, the stirring was continued at 125° C. to yield a nylon salt. The starting materials, reaction conditions and evaluation results of the obtained nylon salt are shown in Table 2.

In any of the production methods of Examples 1 to 22, the dicarboxylic acid can be allowed to react while maintaining the condition of being in powder form, and hence the obtained nylon salt was in powder form and was suitable for solid phase polymerization. In any of the production methods of Examples 1 to 22, the rate of formation of the nylon salt was high, and additionally, the polymerization of the obtained nylon was satisfactory.

In each of Examples 1, 3, 4, 7 and 16 to 22, the diamine was beforehand heated and melted before the reaction, and hence a nylon salt powder having a smaller volume average particle size was able to be obtained in a short time.

In each of Examples 3 and 7, the diamine was beforehand heated and melted before the reaction, the diamine was added while spraying in a spray form, and hence a nylon salt powder having a smaller volume average particle size was able to be obtained in a short time. Additionally, in each of Examples 3 and 7, the rate of formation of the nylon salt was high.

In Example 6, the formation reaction temperature of the nylon salt was higher than the preferable range of the present invention, and hence the particle size of the produced nylon salt powder was slightly larger. Additionally, in Example 6, the rate of formation of the nylon salt was slightly lower. This is inferred to be a result due to partial dissolution of the obtained nylon salt in the water generated by the progress of the amidation reaction.

In Example 10, the addition time of the diamine was shorter than the more preferable range of the present invention, and hence the particle size of the produced nylon salt powder was slightly larger.

In each of Examples 12 and 13, the molar ratio between the diamine and the dicarboxylic acid was outside the preferable range of the present invention. In each of Examples 12 and 13, the nylon salt powder of the present invention was able to be produced, but the relative viscosity of the nylon was slightly lower.

In each of Examples 14, 15, and 17 to 20, when the starting materials were placed in the reaction vessel, water was added to the reaction system; however, the content of water was 5% by mass or less in relation to the total amount of the dicarboxylic acid powder and the diamine, and hence the obtained nylon salt was in powder form and was suitable for solid phase polymerization. Additionally, in each of Examples 14, 15, and 17 to 20, the rate of formation of the nylon salt was high and the polymerization of the nylon was also satisfactory.

In Examples 21 and 22, the reactions were performed in the same manner as in Example 1 except that the polymerization catalyst and the terminal blocking agent in Example 1 were omitted, respectively. As compared to Example 1, Example 21 was slightly lower in the relative viscosity of the nylon, and as compared to Example 1, Example 22 was slightly higher in the relative viscosity of the nylon.

In Comparative Example 1, the diamine was placed in a lump to be added to the dicarboxylic acid powder. Thus, the mixture of the dicarboxylic acid and the diamine became a slurry solution, the dicarboxylic acid was not able to maintain the condition of being in powder form, and with the production of the nylon salt, the whole of the dicarboxylic acid powder agglomerated.

In Comparative Example 2, the reaction temperature was higher than the melting point of the dicarboxylic acid, and hence when the diamine was added, the dicarboxylic acid turned into a solution and was not able to maintain the condition of being in powder form. Therefore, with the production of the nylon salt, the whole of the dicarboxylic acid powder agglomerated.

In Comparative Example 3, the dicarboxylic acid powder was not beforehand heated, and hence the obtained nylon salt became an admixture of agglomerate and powder.

In Comparative Example 4, when the starting materials were placed in the reaction vessel, the amount of water in the reaction system was 7% by mass to be excessive as compared to the range specified in the present invention, and hence the powder was partially dissolved and fused, to yield a nylon salt as an admixture of agglomerate and powder.

INDUSTRIAL APPLICABILITY

According to the method for producing a nylon salt powder of the present invention, the content of water is set at 5% by mass or less in relation to the total amount of the dicarboxylic acid powder and the diamine, and the dicarboxylic acid powder and the diamine are allowed to react with each other while the dicarboxylic acid powder is maintaining the condition of being in powder form; consequently, a nylon salt in a powder form can be obtained without making the steps complicated and leading to cost increase. Additionally, according to the method for producing nylon of the present invention, by polymerizing the nylon salt in a powder form, nylon being excellent in heat resistance and having a high molecular weight can be efficiently obtained. Thus, the method for producing nylon of the present invention is extremely useful.

The invention claimed is:

1. A method for producing a nylon salt powder comprising:
heating a dicarboxylic acid powder to a temperature equal to or higher than the melting point of a diamine and equal to or lower than the melting point of the dicarboxylic acid, and,
while the heating temperature is being maintained, adding the diamine to the dicarboxylic acid powder in such a way that the dicarboxylic acid powder maintains a condition of being in powder form, and
reacting the dicarboxylic acid powder and the diamine to produce nylon salt powder,
wherein the dicarboxylic acid powder and the diamine contain water in an amount of 5% by mass or less.

2. The method for producing a nylon salt powder according to claim 1, wherein the heating temperature is set at 100 to 210° C.

3. The method for producing a nylon salt powder according to claim 1, wherein the diamine is heated to a temperature equal to or higher than the melting point of the diamine, and is sprayed onto the dicarboxylic acid powder.

4. The method for producing a nylon salt powder according to claim 1, wherein a dicarboxylic acid constituting the dicarboxylic acid powder is terephthalic acid and/or isophthalic acid.

5. The method for producing a nylon salt powder according to claim 1, wherein an addition rate of the diamine is 0.07 to 6.7% by mass/min in relation to a total amount of the diamine eventually added.

6. A method for producing nylon comprising producing a nylon salt powder according to the method of claim 1, and polymerizing the nylon salt powder.

* * * * *